United States Patent [19]

Shiozawa et al.

[11] Patent Number: 5,238,678
[45] Date of Patent: Aug. 24, 1993

[54] DOUBLE-COAT TYPE MAKE-UP COSMETIC PRODUCT CONTAINING ALUMINUM POWDER

[75] Inventors: Junji Shiozawa; Kazuhiro Nishikata; Naoki Nakamura, all of Shizuoka, Japan

[73] Assignee: Pola Chemical Industries, Inc., Shizuoka, Japan

[21] Appl. No.: 843,445

[22] Filed: Feb. 28, 1992

[30] Foreign Application Priority Data

Jul. 19, 1991 [JP] Japan .................................. 3-79908
Aug. 28, 1991 [JP] Japan .................................. 3-216985

[51] Int. Cl.⁵ ..................... A61K 7/021; A61K 31/74
[52] U.S. Cl. ................................. 424/63; 424/78.03; 514/844; 523/105
[58] Field of Search ............... 523/105; 526/318.4, 526/330, 936; 524/437; 424/63, 78.03; 514/844

[56] References Cited

U.S. PATENT DOCUMENTS 4,914,140  4/1990  Saitoh et al. .................... 523/105

FOREIGN PATENT DOCUMENTS

| | | |
|---|---|---|
| 9692 | 3/1985 | Japan . |
| 0112709 | 6/1985 | Japan . |
| 12884 | 4/1986 | Japan . |
| 1161211 | 7/1986 | Japan . |
| 45607 | 10/1986 | Japan . |
| 203313 | 8/1989 | Japan . |
| 304015 | 12/1990 | Japan . |
| 2304015 | 12/1990 | Japan . |
| 1447254 | 8/1976 | United Kingdom . |

Primary Examiner—Paul R. Michl
Assistant Examiner—Tae H. Yoon
Attorney, Agent, or Firm—Knobbe, Martens, Olson & Bear

[57] ABSTRACT

Disclosed are a make-up cosmetic product containing, as a film-forming agent, a copolymer with a mean molecular weight of from 10,000 to 1,000,000, as prepared by copolymerizing an acrylate and a polymerizing carboxylic acid at a determined ratio or by copolymerizing an acrylate, at least one selected from vinyl acetate, methyl methacrylate and acrylamide and a polymerizing carboxylic acid at a determined ratio; and a double-coat type make-up cosmetic product comprising, a combination of an under make-up base for a first layer containing as a main component an adhesive film-forming agent such as said copolymer and a finishing make-up material for a second layer containing as a main component an aluminum powder.

5 Claims, No Drawings

DOUBLE-COAT TYPE MAKE-UP COSMETIC PRODUCT CONTAINING ALUMINUM POWDER

BACKGROUND OF THE INVENTION

1. Field of the Invention

The present invention relates to a make-up cosmetic product containing an acrylic copolymer and provides a make-up cosmetic product which is excellent in the ability of fast fixation onto the skin and the ability of well lasting on the skin and which may be easily applied onto the skin by repetitive application.

The present invention also relates to a double-coat type make-up cosmetic product which is composed of an under make-up base as a first layer and a finishing make-up material as a second layer and which is suitable especially for covering and masking various skin troubles.

2. Description of the Prior Art

Hitherto, some make-up cosmetic products containing polymers have been known. These are to have excellent water-proofness, oil-proofness and wear resistance due to the characteristic of the film formed by the polymers.

As examples of such polymers, there are mentioned polyvinyl pyrrolidone, polyacrylamide, polyvinyl acetate, silicone resins (excepting those having a three-dimensional structure), carboxyvinyl polymer and polyvinyl alcohol.

However, the actual use of these make-up cosmetic products is followed by a feeling of sensual and physical disorder (tightness or stretched feeling) since the film formed after drying is lacking in softness. In addition, since the adhesiveness or tackiness of the film formed on the skin is poor, the make-up cosmetic product would often lift up or peel off from the skin to cause unshapeliness of the make-up therewith because of the motion of the skin to follow the movement of the expression muscle such as smiling. Because of the reasons, the make-up cosmetic products have a drawback that any other make-up cosmetic products could not be applied thereover by repetitive application. These drawbacks are extremely serious problems in the make-up cosmetic products of these days, as sensual and physical functions such as the touch and the feeling in use are regarded as important.

For instance, make-up cosmetic products containing synthetic water-soluble polymers (such as carboxyvinyl polymer, polyvinyl alcohol, xanthane gum) have poor water-proofness to often cause unshapeliness of the make-up therewith.

The above-mentioned silicone resins lack in adhesiveness thereof to the skin and therefore have a poor ability of fixation onto the skin.

Three-dimensional network structure-having silicones could be adhesive to the skin in some degree but, after having been applied, the film formed on the skin would be softened due to the sebum secreted therefrom with the lapse of time to thereby often cause a feeling of sensual and physical disorder (stickiness, glossness).

The films formed by polyvinyl pyrrolidone, polyvinyl acetate and polyacrylamide are noticeably hardened also to cause a feeling of sensual and physical disorder such as tightness. In addition, these polymers have additional drawbacks that repetitive application of other cosmetic materials thereover is impossible and that they often peel off due to the motion of the skin.

Make-up cosmetic products containing acrylic copolymers are known. For instance, JP-A 1-203313 (the term "JP-A" as used herein means an "Laid-Open Japanese Patent Publication") has disclosed a make-up cosmetic product comprising a copolymer emulsion made from a mixture of an acrylate with a methacrylate, as a main monomer component, and a glycol of a certain kind, for the purpose of improving mainly the water-proofness of the above-mentioned drawbacks.

On the other hand, as make-up cosmetic products for covering and masking so-called skin troubles such as nevi, spots and freckles or for sun-screening, ones containing titanium dioxide as a white pigment are mainly used.

However, such titanium dioxide-containing make-up cosmetic products have a limited covering power (or light-shielding power). Therefore, although they have an effect for covering and masking slight skin troubles, they are almost ineffective to heavy skin troubles but rather they would often highlight the affected area of such troubles. In addition, since the coat formed by such a make-up cosmetic product would be thick, a naturally finished appearance could not be obtained. Thus, the make-up cosmetic products of the kind often have various problems.

For instance, in the case of pigmentation skin troubles such as heavy nevi or heavy liver spots, the covering and masking power of conventional titanium dioxide-containing make-up cosmetic products was unsatisfactory for sufficiently covering them. This is because even though the cosmetic products could yield scattering of the transmitted light in the foundation layer, a part of the transmitted light would reach the skin so that reflection of the light from the pigmented area of the affected part could not be evaded. In the case, therefore, the skin troubles could be seen with half an eye even though they are coated with the cosmetic materials. In addition, the make-up cosmetic products have other problems that the ability of fast fixation to the skin and the durability on the skin are still insufficient.

JP-A 2-304015 has proposed a make-up cosmetic product (single-coat type) comprising a mixture of an aluminum powder and a film forming agent. The aluminum powder used in the proposed make-up cosmetic product has excellent covering and masking power. However, the proposed cosmetic product has a problem that the finished make-up with it is a thick and heavy one which is not natural and impairs the natural skin feeling.

SUMMARY OF THE INVENTION

The first object of the present invention is to provide a single-coat type make-up cosmetic product, which may form a film with better softness and fast fixation to the skin than any other conventional make-up cosmetic products containing acrylic copolymers and which may be used with ease for repetitive application of being difficult to do with conventional ones.

The second object of the present invention is to provide a double-coat type make-up cosmetic product, which has higher power to cover and mask skin troubles, better ability of fast fixation to the skin and better durability on the skin than any other conventional make-up cosmetic products containing titanium dioxide or aluminum powder and which may yield a better make-up finish than the latter.

The present inventor earnestly studied for the purpose of overcoming the above-mentioned drawbacks in the prior art and, as a result, has found that a make-up film having excellent softness and adhesiveness may be formed by the use of a copolymer with a specified molecular weight as prepared either by the copolymerization of an acrylate (acrylic ester) and a polymerizing carboxylic acid at a specified copolymerization ratio or by the copolymerization of an acrylate, at least one selected from the group consisting of vinyl acetate, methyl methacrylate and acrylamide and a polymerizing carboxylic acid at a specified copolymerization ratio, and additionally has found that a make-up coat (film) having excellent covering and masking power due to the light-shielding effect and also having improved fast fixation to the skin and durability on the skin with satisfactory make-up finish can be obtained by applying an under make-up base containing an adhesive film-forming agent to the affected part with skin troubles to form a first layer on the part followed by further applying a finishing make-up material containing an aluminum powder onto the first layer to form a second layer thereon. On the basis of the findings, the inventor has completed the present invention.

The first invention to attain the first object is as follows:

A make-up cosmetic product containing from 0.1 to 60% by weight, based on the total weight of the cosmetic product, of a copolymer with a mean molecular weight of from 10,000 to 1,000,000 as prepared by the copolymerization of an acrylate as a main monomer component and from 1 to 10% by weight, based on the main monomer component, of a polymerizing carboxylic acid as a side monomer component (hereinafter said copolymer being referred to as "copolymer A") or a copolymer with a mean molecular weight of from 10,000 to 1,000,000 as prepared by the copolymerization of an acrylate as a main monomer component, at least one selected from the group consisting of vinyl acetate, methyl methacrylate and acrylamide as a first side monomer component and from 1 to 10% by weight, based on the total weight of the main monomer component and the first side monomer component, of a polymerizing carboxylic acid as a second side monomer component (hereinafter said latter copolymer being referred to as "copolymer B").

The second invention to attain the second object is as follows:

A double-coat type make-up cosmetic product comprising a combination of an under make-up base for a first layer containing an adhesive film-forming agent and a finishing make-up material for a second layer containing an aluminum powder.

DETAILED DESCRIPTION OF THE INVENTION the first invention and the second invention will be explained in detail hereunder.

FIRST INVENTION

The make-up cosmetic product of the first invention is characterized by the film-forming agent therein, which contains a copolymer A composed of an acrylate as a main monomer component and a polymerizing carboxylic acid as a side monomer component or contains a copolymer B composed of an acrylate as a main monomer component along with at least one selected from the group consisting of vinyl acetate, methyl methacrylate and acrylamide as a first side monomer component and a polymerizing carboxylic acid as a second side monomer component. Both copolymers A and B have a mean molecular weight falling within the range of from 10,000 to 1,000,000. The amount of the polymerizing carboxylic acid as the side monomer component in the former copolymer A is from 1 to 10% by weight, based on the main monomer component; and that of the polymerizing carboxylic acid as the second side monomer component in the latter copolymer B is from 1 to 10% by weight, based on the total of the main monomer component and the first side monomer component. In the latter copolymer B, the ratio of the main monomer component to the first side monomer component is not specifically defined, but it is preferably within the range of from 99/1 to 70/30, by weight. The first side monomer component is used for the purpose of improving the softness and adhesiveness of the film to be formed. If the amount of it is too much, the cohesive force of the copolymer B would be too large so that the softness and adhesiveness of the film to be formed would lower.

As examples of the acrylate, there are mentioned methyl acrylate, ethyl acrylate, propyl acrylate, butyl acrylate, isobutyl acrylate, hexyl acrylate and 2-ethylhexyl acrylate, which may be used singly or in combination of two or more of them.

The polymerizing carboxylic acid may be an unsaturated lower carboxylic acid, including, for example, acrylic acid, methacrylic acid, itaconic acid and maleic acid. These can be used singly or in combination of two or more of them.

As commercial products of the above-mentioned copolymer A and copolymer B, there are mentioned SE-753A and 3LX-174 (trade names by Taisei Chemical Industry Co.).

Next, the film-forming characteristic of the copolymers A and B will be mentioned hereunder.

EVALUATION OF FILM CHARACTERISTIC OF COPOLYMER A

Various copolymer A's were prepared by varying the amount of the polymerizing carboxylic acid and the molecular weight of the copolymer formed, and samples of containing them were examined with respect to the film characteristic.

As the acrylate was used ethyl acrylate; and as the polymerizing carboxylic acid was used acrylic acid. Copolymers were prepared from them, with varying the ratio of the two, and were used in the following experiments.

Samples for evaluation were prepared by mixing 50%, based on the total weight of each sample, of a copolymer, 5% of talc for sensual evaluation, 0.5% of yellow iron oxide and 44.5% of pure water, and these were examined with respect to the following evaluation matters.

(1) Adhesiveness to skin:

Each sample was applied onto the skin and a slide glass. After 10 minutes, the adhesiveness of the film formed to the skin was sensually evaluated by the use of a spatula.

(2) Water-proofness:

Each sample was applied onto the skin. After 10 minutes, the skin of the applied part was rubbed with fingers 20 times each as a back-and-forth motion with a constant force, with applying a running water of a temperature of 40° C. thereto, whereupon the feeling of the skin was sensually evaluated as to whether the sample still remained thereon or not.

(3) Oil-proofness:

Each sample was applied onto the skin. After 10 minutes, the skin of the applied part was rubbed by the use of a piece of cut absorbent cotton for make-up use, into which squalane had been infiltrated, 10 times each as a back-and-forth motion with a constant force, whereupon the feeling of the skin was sensually evaluated as to whether the sample still remained thereon or not.

(4) Softness:

Each sample was applied onto the skin. After 10 minutes, the softness of the coat formed was sensually evaluated by the panelists as to the tightness and stretched feeling, if any, of the coat.

(5) Easiness of repetitive application:

Each sample was applied onto the skin. After 10 minutes, a commercial powder foundation was applied thereover, whereupon the easiness of the repetitive application was sensually evaluated. Application and evaluation were conducted by beauty experts.

The results of evaluation on the above-mentioned matters (1) to (5), based on the following criteria, are shown in Table 1 below.

⊙ : Excellent
◯: Good
△: Fair
×: Bad.

the acrylate and polymerizing carboxylic acid, the same ones as those used in the above-mentioned case of copolymer A's were used. As the first side monomer component were used anyone of vinyl acetate, methyl methacrylate and acrylamide. Copolymer B's were prepared by varying the amounts of these main monomer components, first side monomer component and second side monomer component, and were used in the experiments. The results obtained are shown in Table 2 below.

TABLE 2

| Main Monomer Component | Side Monomer Components | Adhesiveness | Water-proofness | Oil-proofness | Softness | Ability of Repetitive Application |
|---|---|---|---|---|---|---|
| more than 99% | less than 1% | △ | △ | △ | × | × |
| 95% | 5% | ◯ | ◯ | △ | ◯ | △ |
| 90% | 10% | ⊙ | ◯ | ◯ | ◯ | ⊙ |
| 85% | 15% | ⊙ | ⊙ | ◯ | ◯ | ⊙ |
| 80% | 20% | ⊙ | ⊙ | ◯ | ◯ | ⊙ |
| 75% | 25% | ◯ | ⊙ | ◯ | ◯ | ◯ |
| 70% | 30% | ◯ | ◯ | ◯ | ◯ | ◯ |
| less than 70% | more than 30% | × | △ | ◯ | △ | × |

From the results, it was understood that the copolymer B is preferably one as prepared by copolymerizing an acrylate of main monomer component and the first side monomer component and from 1 to 10% by weight, based on the total of the main monomer component and the first monomer component, of the second side monomer component, like the case of the above-mentioned copolymer A, and having a mean molecular weight of from 10,000 to 1,000,000. It was also understood that the optimum ratio of the main monomer component to the first side monomer component is within the range of from 99/1 to 70/30, by weight.

Next, the film characteristic of a copolymer which satisfies the above-mentioned conditions was compared with that of conventional film-forming agents. The copolymer tested was prepared by copolymerizing 98.5% by weight of a mixture of ethyl acrylate and

TABLE 1

| Polymerizing Carboxylic Acid | Molecular Weight of Polymer | Adhesiveness | Water-proofness | Oil-proofness | Softness | Ability of Repetitive Application |
|---|---|---|---|---|---|---|
| less than 1% | less than 10,000 | △ | × | × | ⊙ | ◯ |
| less than 1% | 10,000 to 1,000,000 | ◯ | × | ◯ | ⊙ | △ |
| less than 1% | more than 1,000,000 | ◯ | △ | ◯ | ◯ | × |
| 1% to 10% | less than 10,000 | △ | × | × | ⊙ | ◯ |
| 1% to 10% | 10,000 to 1,000,000 | ⊙ | ⊙ | ⊙ | ⊙ | ⊙ |
| 1% to 10% | more than 1,000,000 | ◯ | ⊙ | ◯ | ◯ | × |
| more than 10% | less than 10,000 | △ | × | × | ◯ | ◯ |
| more than 10% | 10,000 to 1,000,000 | ⊙ | × | △ | △ | △ |
| more than 10% | more than 1,000,000 | ◯ | △ | △ | × | × |

From the results in Table 1 above, it is understood that the copolymer A is preferably one as obtained by copolymerizing an acrylate and from 1 to 10% by weight, based on the acrylate, of a polymerizing carboxylic acid and having a mean molecular weight of from 10,000 to 1,000,000.

EVALUATION OF FILM CHARACTERISTIC OF COPOLYMER B

The same tests of various copolymer B's were carried out with respect to the film-forming characteristic. As butyl acrylate as acrylates (ethyl acrylate/butyl acrylate=4/1) and 1.5% by weight of acrylic acid as a polymerizing carboxylic acid, and it has a mean molecular weight of 100,000. The copolymer had a glass transition temperature of −35° C. This was also used in the following examples. This was called copolymer I.

Preparation of comparative samples and evaluation of the characteristics of the samples were effected in the same manner as mentioned above. The results obtained are shown in Table 3 below.

TABLE 3

| | Adhesiveness | Water-proofness | Oil-proofness | Softness | Ability of Repetitive Application | Total Evaluation |
|---|---|---|---|---|---|---|
| Polyvinyl Pyrrolidone | × | △ | △ | ◯ | △ | △ |
| Polyacrylamide | △ | ◯ | △ | × | × | × |
| Polyvinyl Acetate | ◯ | ⊙ | ◯ | △ | △ | ◯ |

TABLE 3-continued

| | Adhesiveness | Water-proofness | Oil-proofness | Softness | Ability of Repetitive Application | Total Evaluation |
|---|---|---|---|---|---|---|
| Silicone Resin | X | ⊚ | ⊚ | △ | X | △ |
| High Polymer Silicone Oil | X | ⊚ | ◯ | ◯ | X | △ |
| Three-dimensional Network Structure Silicone | ⊚ | ⊚ | △ | ◯ | △ | ◯ |
| Carboxyvinyl Polymer | X | X | △ | ⊚ | △ | X |
| Polyvinyl Alcohol | X | X | △ | ◯ | △ | △ |
| Copolymer I | ⊚ | ⊚ | ⊚ | ⊚ | ⊚ | ⊚ |

From the results, it was understood that the copolymer of the present invention may form a make-up coat having no sensual feeling disorder and having higher softness and adhesiveness, better water-proofness and oil-proofness and higher easiness of repetitive application, when incorporated into a make-up cosmetic product, than any other polymers of conventional film forming agents.

The make-up cosmetic product of the first invention may have any form of any type, provided that it contains the above-mentioned copolymer. For instance, it may be an under make-up base of an emulsion type, a cream type, an aqueous gel type or a high concentration type; or may also be a finishing make-up material for foundation or control color.

Accordingly, the make-up cosmetic product of the first invention may be composed of the same components as those in conventional make-up cosmetic products except the film-forming agent.

The constitutive components of the make-up cosmetic product of the first invention, when used as an under make-up base, will be mentioned. Where it is in the form of an under make-up base of an emulsion type or cream type, in general, the base components are oily components of forming an oily phase, which comprises (1) at least one selected from the group consisting of higher fatty acids (e.g., stearic acid, palmitic acid, myristic acid, lauric acid, and esters thereof), higher alcohols (e.g., cetanol, lanolin alcohol, stearyl alcohol, cetostearyl alcohol) and waxes (e.g., solid paraffin, microcrystalline wax, ceresine wax, polyethylene wax, bees wax, Japan wax, carnauba wax, candelilla wax), and (2) at least one selected from natural or synthetic oily substances (e.g., squalane, liquid paraffin, lanolin or its derivatives, olive oil, camellia (tsubaki) oil, cotton seed oil, oleyl alcohol, castor oil, vaseline, diethoxyethyl adipate, silicone oil); aqueous components of (1) a moisturizing agent (e.g., polyalcohols such as glycerin, propylene glycol, 1,3-butylene glycol, sorbitol and its derivatives, polyethylene glycol), (2) a film-forming agent of a copolymer A and/or a copolymer B, and (3) water (pure water); and an emulsifying agent for homogenizing the above-mentioned oily components and aqueous components (e.g., surfactants such as polyoxyethylene oleate, polyoxyethylene cetyl ether, aluminum stearate, octyl dodecanol, oleophilic glycerin monostearate, propylene glycol monostearate). The emulsion type under make-up base and the cream type under make-up base are differentiated from each other in the content of the liquid component such as water therein. Briefly, the former contains more liquid component than the latter. To the under make-up base of every type, may be added various additives such as an antiseptic (e.g., para-hydroxybenzoic acid and its esters such as paraben, methylparaben, butylparaben), a colorant, a keratin softening agent (e.g., alkali substances such as triethanolamine, potassium hydroxide, potassium carbonate), a tackifier (e.g., carboxyvinyl polymer, CP jelly), a microbicidal solvent (e.g., lower alcohols such as ethanol, propanol, isopropanol), a perfume, a nutrient (e.g., amino acids, vitamins), an antioxidant (e.g., dibutylhydroxytoluene), etc.

An under make-up base of an aqueous gel type or high concentration type may comprise, in general, the above-mentioned aqueous components except the oily components and the emulsifying agent, or it may comprise as essential components a moisturizing agent; a copolymer A and/or a copolymer B; water; and a lower alcohol, or it may also comprise as an essential component(s) a copolymer A and/or a copolymer B. In addition, the above-mentioned additives may be added thereto. The aqueous gel type under make-up base and the high concentration type under make-up base are differentiated from each other in the content of the film-forming agent therein. Briefly, the former contains more film-forming agent than the latter.

Next, the constitutive components of the make-up cosmetic product of the first invention, when used as a finishing make-up material, will be mentioned. Both the foundation type finishing make-up material and the control color type finishing make-up material are basically composed of the above-mentioned oily components, aqueous components and emulsifying agent as essential components, like the emulsion type or cream type under make-up base, except that they additionally contain a colorant (generally, comprising pigments for finishing make-up materials). In addition to them, the above-mentioned additives may also be added to these finishing make-up materials. Pigments to be used in the finishing make-up materials are generally in the form of combination of white pigment(s) and color pigment(s). As white pigments, usable are, for example, titanium oxide, kaolin, talc, bentonite, mica and nylon powder; and as color pigments, usable are, for example, red iron oxide, yellow iron oxide, black iron oxide and ultramarine. These finishing make-up materials are differentiated from the emulsion type or cream type under make-up base especially in the content of water therein, in addition to the presence or absence of pigments therein. Briefly, the former finishing make-up materials contain less water than the latter under make-up bases. The foundation type finishing make-up material and the control color type one are basically almost same with respect to the main components but they are different from each other only with respect to the kind of the pigments therein.

The content of above-mentioned copolymer in the make-up cosmetic product of the first invention may vary within the range of from 0.1 to 60% in accordance with the form (emulsion type, cream type etc.) of itself. If it is too small, as overstepping the defined range, the effect of forming a make-up coat (film) with excellent feeling in use could not be expected. On the contrary, if it is too much, the make-up coat to be formed would be unfavorably too hard. Anyhow, the larger the copolymer content within the defined range, the higher the hardness of the make-up coat to be formed. Thus, the desired hardness of a make-up coat to be formed by a make-up cosmetic product varies in accordance with the use object. The make-up cosmetic product of the present invention may form a make-up coat with a desired hardness by varying the copolymer content therein. Contents of other components in the make-up cosmetic product of the present invention may vary widely in accordance with the form of itself, like conventional make-up cosmetic products. Amounts of other components in the make-up cosmetic product of the present invention could not be specifically defined, since they broadly vary in accordance with the form of the cosmetic product.

For producing the make-up cosmetic product of the first invention, any and every known technology of producing conventional make-up cosmetic products may be employed. For instance, for producing the material of an under make-up base of an emulsion type or cream type, oily components of higher fatty acids and higher alcohols are blended and, if desired, heated, then aqueous components of a suspension of the above-mentioned copolymer and a moisturizing agent are added thereto along with an emulsifying agent, and the whole is emulsified and dispersed to form an emulsified dispersion.

It is recommended to use the make-up cosmetic product of the first invention as an under make-up base and to overcoat a finishing make-up material such as powder foundation, emulsion foundation or face powder over the under make-up base, whereupon there is obtained a double coated make-up film which may well last, which is hardly transferred to a wearing suit or others, and which is an ideal one.

The make-up cosmetic product of the first invention may form a make-up coat with excellent softness and adhesiveness and is characterized by the ability of fast fixation to the skin and the durability on the skin and also by the easiness of repetitive application of plural make-up cosmetic products.

SECOND INVENTION

The second invention is a double-coat type make-up cosmetic product comprising a combination of an under make-up base for a first layer, which is directly applied to the skin, and a finishing make-up material for a second layer, which is coated over the first layer. The under make-up base for the first layer contains an adhesive film-forming agent, and the finishing make-up material for the second layer contains an aluminum powder.

The adhesive film-forming agent in the under make-up base has the ability to improve not only the fast fixation of the first layer to the skin but also the fast fixation, adhesiveness and durability of the aluminum power used in the second layer over the first layer. In addition, it is used for the purpose of forming a thin light-shielding make-up coat and of preventing from impairing a natural skin appearance.

The adhesive film-forming agent for use in the present invention is desired to have the following physical properties, when tested as an adhesive tape by the method of JIS Z-0237.

Tack: 5 to 20
Adhesive strength (to stainless steel plate): 500 to 2000 g/25 mm.

The adhesion test methods are as follows. Precisely, an adhesive film-forming agent sample to be tested is coated on a release paper and dried thereon, this is stuck to a coated paper, the release paper is peeled off therefrom to give an adhesive tape, and the adhesive tape is tested in accordance with the following methods:

Test Methods:
Tack:
Tack is tested by the test method of JIS Z-0237.
Adhesive strength:
This is an adhesive strength (g/25 mm) as determined by a 180-degree peeling test defined by JIS Z-0237, using a stainless steel plate as an object to which the adhesive tape to be tested is stuck.

As specific examples of the adhesive film-forming agent having such adhesive properties, there are mentioned the copolymers A and B used in the first invention; and three-dimensional network structure-having silicones. Preferred are the copolymers A and B.

Three-dimensional network structure-having silicones usable in the second invention are obtained, for example, by hydrolyzing organic trichlorosilanes ($RSiCl_3$) and organic dichlorosilanes ($RSiCl_2$) followed by condensing and cross-linking them. As a commercial product, there is known Silicone KF7613B (product by Shin-Etsu Chemical Co.).

The under make-up base for the first layer may be anyone of any type, provided that it contains an adhesive film-forming agent. It includes, for example, various under make-up bases of various constitutions such as emulsion type, cream type, aqueous gel type or high concentration type ones, like the first invention. For instance, there is typically mentioned a high concentration type under make-up base comprising, as a main component, the above-mentioned adhesive film-forming agent, water, a lower alcohol and a moisturizing agent. The content of the adhesive film-forming agent in the first layer is generally within the range of from 0.5 to 70% by weight, based on the total weight of the under make-up base for the first layer, though varying in accordance with the form of the under make-up base of itself.

The under make-up base for the first layer may contain any other ordinary additives for conventional make-up cosmetic products such as those mentioned for the aforesaid first invention.

The finishing make-up material for the second layer of the second invention is used as one for forming a second layer (foundation or control color) to be coated over the first layer from above-mentioned the under make-up base. The finishing make-up material contains an aluminum powder. The aluminum powder therein is used for the purpose of improving the covering and masking power of the second layer for shielding skin troubles. The aluminum powder content in the finishing make-up material is generally from 5 to 100% by weight, preferably from 5 to 40% by weight, based on the total weight of the material.

If the aluminum powder content in the second layer is less than 5% by weight, the covering and masking power would lower. If, on the contrary, it is more than 40% by weight, application of an ordinary finishing make-up foundation over the second layer to form a third layer thereon would be desired.

The aluminum powder used in the second layer generally has a mean grain size of from 10 to 70 $\mu$m, preferably from 20 to 50 $\mu$m. If the mean grain size is less than 10 $\mu$m, the aluminum powder of itself would be dull so that the make-up finish would be sensually unacceptable. If, on the contrary, it is more than 70 μm, the material would be rough to cause a feeling of sensual and physical disorder.

The finishing make-up material for the second layer may contain, in addition to an aluminum powder, any other additives of oily components, aqueous components, emulsifier, colorant (generally, pigments), water, perfume and nutrient, such as those mentioned for the first invention, in such amounts that would not lower the covering and masking power of the layer. For instance, the material typically contains an aluminum powder, oily substances and a colorant (white pigments and color pigments).

The double-coat type make-up cosmetic product of the second invention is excellent in the ability of covering and masking skin troubles and additionally it forms a make-up coat having improved adhesiveness, durability and finish appearance.

DESCRIPTION OF THE PREFERRED EMBODIMENT

The present invention will be explained in more detail by way of the following examples. Examples 1 to 7 demonstrate the embodiments of the first invention; and Examples 8 to 11 demonstrate those of the second invention. In Examples 1, 2 and 4 to 8, the above-mentioned copolymer I was used. Precisely, the copolymer I was one as prepared by copolymerizing 98.5% by weight of a mixed monomer comprising ethyl acrylate and butyl acrylate (the ratio of the former to the latter being 4/1) and 1.5% by weight of acrylic acid and had a mean molecular weight of 100,000 and a glass transition temperature of −35° C. Regarding the adhesive properties of the copolymer, it had a tack value of 17 and an adhesive strength of 1500 g/25 mm.

In Example 3, a copolymer as prepared by copolymerizing 96.5% by weight of a mixed monomer comprising ethyl acrylate and butyl acrylate (the ratio of the former to the latter being 4/1), 2.0% by weight of methyl methacrylate and 1.5% by weight of acrylic acid was used. The copolymer had a mean molecular weight of 100,000 and a glass transition temperature of −25° C. The copolymer was .ojoff-called copolymer II.

The three-dimensional network structure silicone used hereunder was one as prepared, for example, in accordance with the disclosure of JP-A 61-18708 (applicant: Pola Chemicals Co.), and it had a tack value of 10 and an adhesive strength power of 1000 g/25 mm.

EXAMPLE 1

This is to compare an emulsion type under make-up base sample containing a copolymer of the present invention (Example 1) and a comparative sample of a conventional under make-up base containing a vinyl acetate polymer (Comparative Example 1).

METHOD OF PRODUCING SAMPLES

Components of A in Table 3 were previously heated up to 85° C., and components of B in the same table also previously heated up to 87° C. or higher were gradually added thereto little by little with stirring, and the whole was emulsified. Then, it was cooled to 40° C. still with stirring to obtain a sample product.

The final content of the copolymer of the invention in the sample was 10%.

TABLE 4

| Components | Example 1 (%) | Comparative Example 1 (%) |
|---|---|---|
| A | | |
| Stearic Acid | 0.2 | 0.2 |
| Cetanol | 1.5 | 1.5 |
| Vaseline | 3.0 | 3.0 |
| Lanolin Alcohol | 2.0 | 2.0 |
| Liquid Paraffin | 10.0 | 10.0 |
| Polyoxyethylene-monooleate | 2.0 | 2.0 |
| Butylparaben | 0.2 | 0.2 |
| B | | |
| Glycerin | 3.0 | 3.0 |
| Propylene Glycol | 5.0 | 5.0 |
| Triethanolamine | 1.0 | 1.0 |
| Copolymer I (50% aqueous suspension) | 20.0 | — |
| Polyvinyl Acetate (50% aqueous suspension) | — | 20.0 |
| Methylparaben | 0.2 | 0.2 |
| Pure Water | 51.9 | 51.9 |

EVALUATION

Both the under make-up base samples of Example 1 and Comparative Example 1 were tested with respect to the disorder feeling of the film as formed, the lastability of the make-up coat, the water-proofness and the easiness of repetitive application. For the tests, each sample was applied to the face of each of 15 women panelists and was sensually evaluated by them on the basis of the following criteria.

Criteria for sensual evaluation:
⊙ : Excellent
○: Good
△: Fair
×: Bad.

The results obtained are shown in Table 5 below.

TABLE 5

| | Feeling of make-up coat after dried | Lastability of make-up coat | Water-proofness | Easiness of repetitive application |
|---|---|---|---|---|
| Example 1 | ⊙ | ⊙ | ○ | ⊙ |
| Comparative Example 1 | ○ | △ | × | △ |

From the results, it was understood that the under make-up base sample containing the copolymer of the present invention (Example 1) was superior to the comparative sample containing the conventional vinyl acetate copolymer (Comparative Example 1) with respect to all the tested matters.

EXAMPLE 2

This demonstrates use of cream type under make-up base samples.

METHOD OF PRODUCING SAMPLES

Components of A in Table 6 below were mixed and heated up to 70° C. Components of B, C and D including emulsifying agent and perfume were mixed and melted by heating up to 70° C., and the resulting melt was added to the mixture of the components of A. The whole was pre-emulsified and then uniformly emulsified with a homogenizing mixer. The emulsion was then cooled to room temperature with a heat exchanger to obtain a sample product. The final content of the copolymer of the invention in the sample was 1.5%.

TABLE 6

| Components | Example 2 (%) | Comparative Example 2 (%) |
|---|---|---|
| A | | |
| Methylparaben | 0.2 | 0.2 |
| Propylene Glycol | 5.0 | 5.0 |
| Pure Water | 64.3 | 64.3 |
| Copolymer I (50% aqueous suspension) | 3.0 | — |
| Xanthane Gum | — | 3.0 |
| B | | |
| Butylparaben | 0.2 | 0.2 |
| Stearyl Alcohol | 7.0 | 7.0 |
| Stearic Acid | 2.0 | 2.0 |
| Reducing Lanolin | 2.0 | 2.0 |
| Squalane | 5.0 | 5.0 |
| C | | |
| Octyldodecanol | 6.0 | 6.0 |
| Polyoxyethylene Cetyl Ether (25 E.O.) | 3.0 | 3.0 |
| Oleophilic Glycerin Monostearate | 2.0 | 2.0 |
| d | | |
| Perfume | 0.3 | 0.3 |

EVALUATION

Each of the thus prepared cream type under make-up base samples was applied to the face of each of 15 women panelists and was evaluated in the same manner as in Example 1. The use test results obtained are shown in Table 7 below.

TABLE 7

| | Disorder feeling of make-up coat after dried | Lastability of make-up coat | Water-proofness | Easiness of repetitive application |
|---|---|---|---|---|
| Example 2 | ◉ | ◉ | ○ | ○ |
| Comparative Example 2 | ⊙ | △ | △ | × |

From the results, it was understood that the under make-up base sample containing the copolymer of the present invention (Example 2) was superior to the comparative sample containing the conventional xanthane gum (Comparative Example 2) with respect to all the tested matters.

Next, each of the cream type under make-up base samples prepared above was applied to the face of each of 15 women panelists and then a powder foundation as prepared by the method mentioned below was applied thereover by repetitive application. Then, all the panelists were subjected to a wear-resistance test with respect to the make-up coat.

METHOD OF PREPARING POWDER FOUNDATION

Components of A in Table 8 below were mixed in a Henschel mixer and then ground in a hammer mill. To this were added components of B in the same table, and the whole was subjected to finish-grinding again in a hammer mill to finally obtain a powder foundation.

TABLE 8

| Components | Amount (%) |
|---|---|
| A | |
| Talc | 33.69 |
| Sericite | 20.0 |
| Titanium Oxide | 20.0 |

TABLE 8-continued

| Components | Amount (%) |
|---|---|
| Nylon Powder | 5.0 |
| Yellow Iron Oxide | 5.0 |
| Red Iron Oxide | 1.0 |
| Ultramarine | 1.0 |
| B | |
| Paraben | 0.2 |
| Liquid Paraffin | 5.0 |
| Squalane | 5.0 |
| Silicone Oil | 4.0 |
| Perfume | 0.1 |
| Dibutylhydroxytoluene | 0.01 |

WEAR-RESISTANCE TEST

The face as coated with the powder foundation was rubbed with a dry white cloth 10 times by back-and-forth motion, whereupon the amount of the powder foundation as transferred to the cloth was visually measured.

In the test, a large amount of the powder foundation migrated to the cloth when the under make-up base of Comparative Example 2 was used, while almost no powder foundation migrated to it when the under make-up base of Example 2 was used. From the results, it was understood that the wear-resistance of the make-up coat of the powder foundation as applied over the under make-up base of the present invention by repetitive application was improved.

EXAMPLE 3

This demonstrates the use of aqueous gel type under make-up base samples.

METHOD OF PRODUCING SAMPLES:

Components of A in Table 9 below were put in a dissolution cauldron and stirred rapidly with a pulsometer so that the components were solubilized. Then, potassium hydroxide was put therein and stirred, and components of C, which had previously been dissolved in pure water, were added thereto and stirred further. Thus, the resulting system was neutralized to give a sample product. The final content of the copolymer of the invention in the sample was 0.75%.

TABLE 9

| Components | Example 3 (%) | Comparative Example 3 (%) |
|---|---|---|
| A | | |
| Ethanol | 12.0 | 12.0 |
| Polyethylene Glycol 4000 | 1.0 | 1.0 |
| 1,3-Butylene Glycol | 3.0 | 3.0 |
| B | | |
| Potassium Hydroxide | 0.2 | 0.2 |
| C | | |
| Blue No. 1 | 0.0003 | 0.0003 |
| Methylparaben | 0.2 | 0.2 |
| Diethoxyethyl Adipate | 0.4 | 0.4 |
| L-hydroxyproline | 0.01 | 0.01 |
| Carboxyvinyl Polymer | 0.4 | 0.4 |
| CP Jelly | 1.7 | 1.7 |
| Pure Water | 79.5897 | 79.5897 |
| Xanthane Gum | 1.5 | — |
| Copolymer II (50% aqueous suspension) | — | 1.5 |

EVALUATION

Each of the samples prepared as above was applied to the face of 15 women panelists and sensually tested with respect to the feeling of the make-up coat after dried, the water-proofness, the lastability of the make-up coat after foundation was overcoated and the easiness of repetitive application of foundation, on the basis of the following criteria. Criteria for sensual evaluation:
⊚ : Excellent
◯: Good
Δ: Fair
×: Bad.
The results obtained are shown in Table 10 below.

TABLE 10

|  | Fightness feeling of make-up coat after dried | Water- proofness | Lastability of make-up coat as overcoated with foundation | Easiness of repetitive application of foundation over make-up coat |
| --- | --- | --- | --- | --- |
| Example 3 | ⊚ | ⊚ | ⊚ | ⊚ |
| Comparative Example 3 | ◯ | × | × | × |

From the results, it was understood that the under make-up base sample containing the copolymer of the present invention (Example 3) was superior to the comparative sample containing the conventional xanthane gum (Comparative Example 3) with respect to all the tested matters.

EXAMPLE 4

This demonstrates the use of emulsion type control color samples.

METHOD OF PRODUCING SAMPLES

Components of A in Table 11 were previously heated up to 85° C. and those of B in the same table up to 87° C. The latter were gradually added to the former little by little with stirring and emulsified. Stirring was continued further with cooling, and components of C were added to the blend of A and B while it was at 55° to 60° C. Then, the whole was stirred further with cooling until it became 40° C. to obtain a sample product. The final content of the copolymer of the invention in the sample was 11%.

TABLE 11

| Components | Example 4 (%) | Comparative Example 4 (%) |
| --- | --- | --- |
| A |  |  |
| Bees Wax | 2.0 | 2.0 |
| Stearic Acid | 2.5 | 2.5 |
| Liquid Paraffin | 14.0 | 14.0 |
| Oleophilic Glycerin Monostearate | 6.0 | 6.0 |
| Lanolin | 2.0 | 2.0 |
| Color Pigment Paste and White Pigment Paste | 17.0 | 17.0 |
| B |  |  |
| Triethanolamine | 1.0 | 1.0 |
| Glycerin | 4.0 | 4.0 |
| Pure Water | 29.2 | 29.2 |
| Polyvinyl Acetate (50% aqueous suspension) | — | 22.0 |
| Copolymer I (50% aqueous suspension) | 22.0 | — |

TABLE 11-continued

| Components | Example 4 (%) | Comparative Example 4 (%) |
| --- | --- | --- |
| C |  |  |
| Perfume | 0.3 | 0.3 |

EVALUATION

The both emulsion type control color samples prepared as above were tested and evaluated in the same manner as in Examples 1 and 2. The results obtained are shown in Table 12 below.

TABLE 12

|  | Feeling of make-up coat after dried | Lastability of make-up coat | Water- proofness | Easiness of repetitive application |
| --- | --- | --- | --- | --- |
| Example 4 | ⊚ | ⊚ | ◯ | ⊚ |
| Comparative Example 4 | Δ | ◯ | ◯ | × |

From the results, it was understood that the emulsion type control color sample containing the copolymer of the present invention (Example 4) was superior to the comparative sample containing the conventional polyvinyl acetate (Comparative Example 4) with respect to all the tested matters, except that the former was comparable to the latter with respect to the water-proofness.

EXAMPLE 5

This demonstrates the use of emulsion foundation samples.

METHOD OF PRODUCING SAMPLES

Components of C in Table 13 below were well mixed and then ground with a grinder. The thus ground components C were put into the oily phase components of A, which had previously been heated and melted at 80° C., and dispersed with a disper.

After dispersed, the aqueous components of B, which had also been heated and melted at 80° C., were added to the dispersion with stirring, and thereafter the whole was cooled with stirring to 30° C. to obtain a sample product. The final content of the copolymer of the invention in the sample was 7.5%.

TABLE 13

| Components | Example 5 (%) | Comparative Example 5 (%) |
| --- | --- | --- |
| A |  |  |
| Stearic Acid | 2.4 | 2.4 |
| Propylene Glycol Monostearate | 2.0 | 2.0 |
| Cetostearyl Alcohol | 0.2 | 0.2 |
| Liquid Lanolin | 2.0 | 2.0 |
| Liquid Paraffin | 3.0 | 3.0 |
| Isopropyl Myristate | 8.5 | 8.5 |
| Propyl Parahydroxybenzoate | 0.1 | 0.1 |
| B |  |  |
| Pure Water | 45.6 | 45.6 |
| Polyvinyl Alcohol (50% aqueous suspension) | — | 15.0 |
| Copolymer I (50% aqueous suspension) | 15.0 | — |
| Propylene Glycol | 4.0 | 4.0 |
| Triethanolamine | 1.1 | 1.1 |
| Methyl Parahydroxybenzoate | 0.1 | 0.1 |
| C |  |  |

TABLE 13-continued

| Components | Example 5 (%) | Comparative Example 5 (%) |
|---|---|---|
| Titanium Oxide | 8.0 | 8.0 |
| Talc | 4.0 | 4.0 |
| Color Pigment | 4.0 | 4.0 |

EVALUATION

Both the thus prepared emulsion foundation samples were tested and evaluated in the same manner as in Example 4. The results obtained are shown in Table 14 below.

TABLE 14

| | Disorder feeling of make-up coat after dried | Lastability of make-up coat | Water-proofness | Easiness of repetitive application |
|---|---|---|---|---|
| Example 5 | ⊙ | ⊙ | ○ | ○ |
| Comparative Example 5 | ○ | △ | △ | × |

From the results, it was understood that the emulsion foundation sample containing the copolymer of the present invention (Example 5) was superior to the comparative sample containing the conventional polyvinyl alcohol (Comparative Example 5) with respect to all the tested matters.

EXAMPLE 6

This demonstrates the use of other emulsion foundation samples.

METHOD OF PRODUCING SAMPLES

Components of A in Table 15 below were heated at 85° C., melted and dispersed, and components of B, which had previously been heated up to 85° C. with stirring, were gradually added thereto and emulsified. The whole was then stirred for 10 minutes with maintaining the temperature to be the same as that for emulsification. Next, this was cooled to 45° C., whereupon the component C was added thereto with stirring. After cooled to 35° C., a product sample was obtained. The final content of the copolymer of the .ojoffinvention in the sample was 17.5%.

TABLE 15

| Components | Example 6 (%) | Comparative Example 6 (%) |
|---|---|---|
| A | | |
| Stearic Acid | 0.4 | 0.4 |
| Isostearic Acid | 0.3 | 0.3 |
| Isopropyl Myristate | 4.0 | 4.0 |
| Liquid Paraffin | 10.0 | 10.0 |
| Oleophilic Glycerin Monostearate | 4.5 | 4.5 |
| Color Pigment Paste | 17.0 | 17.0 |
| Cetyl Alcohol | 0.3 | 0.3 |
| Dibutylhydroxytoluene | 0.05 | 0.05 |
| Butylparaben | 0.02 | 0.02 |
| B | | |
| Triethanolamine | 0.42 | 0.42 |
| Propylene Glycol | 5.0 | 5.0 |
| Methylparaben | 0.02 | 0.02 |
| Copolymer I (50% aqueous suspension) | 35.0 | — |
| Polyvinyl Alcohol (50% aqueous suspension) | — | 35.0 |
| Pure Water | 22.69 | 22.69 |

TABLE 15-continued

| Components | Example 6 (%) | Comparative Example 6 (%) |
|---|---|---|
| C | | |
| Perfume | 0.3 | 0.3 |

EVALUATION

Both the thus prepared emulsion foundation samples were tested and evaluated in the same manner as in Examples 4 and 5. The results obtained are shown in Table 16 below.

TABLE 16

| | Disorder feeling of make-up coat after dried | Lastability of make-up coat | Water-proofness | Easiness of repetitive application |
|---|---|---|---|---|
| Example 6 | ⊙ | ○ | ○ | ⊙ |
| Comparative Example 6 | △ | ○ | × | ○ |

From the results, it was understood that the emulsion foundation sample containing the copolymer of the present invention (Example 6) was superior to the comparative sample containing the conventional polyvinyl alcohol (Comparative Example 6) with respect to all the tested matters, except that the former was comparable to the latter with respect to the lastability of the make-up coat.

EXAMPLE 7

This demonstrates the use of an under make-up base sample containing the copolymer of the invention in a high concentration.

METHOD OF PRODUCING SAMPLES

Components of A in Table 17 below were stirred and solubilized, and component B in the same table was gradually added thereto little by little with stirring. Thus, a sample product was produced.

The final content of the copolymer of the invention in the sample was 50%.

TABLE 17

| Components | Example 7 (%) | Comparative Example 7 (%) |
|---|---|---|
| A | | |
| Ethanol | 10.0 | 10.0 |
| 1,3-Butylene Glycol | 3.0 | 3.0 |
| Pure Water | 36.8 | 36.8 |
| Methylparaben | 0.2 | 0.2 |
| B | | |
| Polyvinyl Alcohol | — | 50.0 |
| Copolymer I | 50.0 | — |

Evaluation

Both the thus prepared under make-up base samples were tested and evaluated in the same manner as in Examples 4, 5 and 6. The results obtained are shown in Table 18 below.

TABLE 18

| | Disorder feeling of make-up coat after dried | Lastability of make-up coat | Water-proofness | Easiness of repetitive application |
|---|---|---|---|---|
| Example 7 | ⊙ | ⊙ | ○ | ⊙ |
| Comparative Example 7 | △ | △ | × | △ |

From the results, it was understood that the under make-up base sample containing the copolymer of the present invention (Example 7) was superior to the comparative sample containing the conventional polyvinyl alcohol (Comparative Example 7) with respect to all the tested matters. It was further understood that the sample of Example 7 containing the copolymer of the invention in such a high concentration was still excellent with respect to all the tested matters.

EXAMPLE 8

Components of A in Table 19 below were stirred and solubilized, and the component B in the same table was gradually added thereto little by little with stirring to prepare an under make-up base sample for the first layer (hereinafter referred to as "under make-up base sample 1").

TABLE 19

| Components | Amount (%) |
|---|---|
| A | |
| Ethanol | 10.0 |
| 1,3-Butylene Glycol | 3.0 |
| Pure Water | 36.8 |
| Methylparaben | 0.2 |
| B | |
| Copolymer I | 50.0 |

Next, powdery components of A in Table 20 below were mixed in a Henschel mixtuer and then pulverized in a pulverizer. Again the resulting mixture was put in the powder mixture, and oily components of B in the same table were added thereto and mixed, whereupon the powdery mixture of A was coated with the oily mixture of B. The coated mixture was taken out from the mixer and subjected to finish-pulverizing in the pulverizer to prepare a finishing make-up material (powder foundation) for a second layer (hereinafter said finishing make-up material being referred to as "finishing make-up material sample 1"). This was press-shaped in a shallow dish and stored.

TABLE 20

| Components | Amount (%) |
|---|---|
| A | |
| Aluminium Powder (mean grain size 15 μm) | 25 |
| Titanium Dioxide | 20 |
| Talc | 30 |
| Mica | 10 |
| Red Iron Oxide | 1 |
| Ultramarine | 1 |
| Paraben | 0.2 |
| Yellow Iron Oxide | 3 |
| B | |
| Liquid Paraffin | 5 |
| Squalane | 4.8 |

EXAMPLE 9

Under make-up base sample 1 was prepared as an under make-up base sample for a first layer, in the same manner as in Example 8.

Next, a finishing make-up material sample for a second layer was prepared in the same manner as in the preparation of the finishing make-up material sample in Example 8 except that the components as indicated in Table 21 were used, and it was called "finishing make-up material sample 2". This was press-shaped in a shallow dish and stored.

TABLE 21

| Components | Amount (%) |
|---|---|
| A | |
| Aluminium Powder (mean grain size 15 μm) | 70 |
| Titanium Dioxide | 5 |
| Talc | 5 |
| Mica | 5 |
| Red Iron Oxide | 1 |
| Ultramarine | 1 |
| Paraben | 0.2 |
| Yellow Iron Oxide | 3 |
| B | |
| Liquid Paraffin | 5 |
| Squalane | 4.8 |

Further, a finishing make-up material sample for a third layer (powder foundation) was prepared in the same manner as in the preparation of the finishing make-up material sample for the second layer in Example 8 except that the components as indicated in Table 22 were used, and it was called "finishing make-up material sample 3". This was press-shaped in a shallow dish and stored.

TABLE 22

| Components | Amount (%) |
|---|---|
| A | |
| Silica Beads | 10 |
| Titanium Dioxide | 5 |
| Talc | 40 |
| Mica | 30 |
| Red Iron Oxide | 1 |
| Ultramarine | 1 |
| Paraben | 0.2 |
| Yellow Iron Oxide | 3 |
| B | |
| Liquid Paraffin | 5 |
| Squalane | 4.8 |

EXAMPLE 10

Components as indicated in Table 23 below were put in a dissolution cauldron and mixed at room temperature to prepare an under make-up base sample for a first layer (hereinafter said sample being referred to as "under make-up base sample 2")...ls1.

TABLE 23

| Components | Amount (%) |
|---|---|
| Volatile Silicone Oil (viscosity 1 cs) | 50 |
| Dimethylpolysiloxane (viscosity 20 cs) | 2 |
| Three-dimensional Network Structure Silicone | 48 |

On the other hand, finishing make-up material sample 1 for the second layer was prepared in the same manner as in Example 8.

EXAMPLE 11

As an under make-up base sample for a first layer, under make-up base sample 1 of Example 8 was prepared; as a finishing make-up material sample for a second layer, finishing make-up material sample 2 of Example 9 was prepared; and as a finishing make-up material sample for a third layer, finishing make-up material sample 3 of Example 9 was prepared.

COMPARATIVE EXAMPLE 8

An under make-up base sample for a first layer was prepared in the same manner as in Example 1, except that polyvinyl alcohol was used in place of copolymer I. This is called "under make-up base sample 3".

On the other hand, as a finishing make-up material sample for a second layer, finishing make-up material sample 1 of Example 8 was prepared.

COMPARATIVE EXAMPLE 9

As a under make-up base sample for a first layer, under make-up base sample 1 of Example 8 was prepared. On the other hand, a finishing make-up material sample for a second layer (powder foundation) was prepared in the same manner as in Example 8 except that the powdery components of A and the oily components of B as indicated in Table 24 below were used. This is called "finishing make-up material sample 4".

TABLE 24

| Components | Amount (%) |
|---|---|
| A | |
| Silica Beads | 10 |
| Titanium Dioxide | 30 |
| Talc | 15 |
| Mica | 30 |
| Red Iron Oxide | 1 |
| Ultramarine | 1 |
| Paraben | 0.2 |
| Yellow Iron Oxide | 3 |
| B | |
| Liquid Paraffin | 5 |
| Squalane | 4.8 |

COMPARATIVE EXAMPLE 10

As an under make-up base sample for a first layer, under make-up base sample 2 of Example 10 was prepared; and as a finishing make-up material sample for a second layer, finishing make-up material sample 4 of Comparative Example 9 was prepared.

COMPARATIVE EXAMPLE 11

As an under make-up base sample for a first layer, under make-up base sample 3 of Comparative Example 8 was prepared; and as the finishing make-up material sample for the second layer, finishing make-up material sample 4 of Comparative Example 9 was prepared.

COMPARATIVE EXAMPLE 12

Under make-up base sample 3 of Comparative Example 8 was prepared. On the other hand, components of A of Table 25 below were heated and melted and then dispersed in a roll mill. Again the resulting dispersion was heated and melted, and aluminum powder was added thereto and mixed, stirred and homogenized to prepare a finishing make-up material sample (oily foundation). This is called finishing make-up material sample 5.

TABLE 25

| Components | Amount (%) |
|---|---|
| A | |
| Microcrystalline Wax | 10.0 |
| Polyethylene Powder | 5.0 |
| Liquid Paraffin | 15.0 |
| Lanolin | 5.0 |
| Castor Oil | 5.0 |
| Squalane | 8.3 |
| Sorbitan Sesqui-oleate | 1.0 |
| Butylparaben | 0.2 |
| Yellow Iron Oxide | 5.0 |
| Red Iron Oxide | 0.5 |
| Titanium Dioxide | 15.0 |
| B | |
| Aluminium Powder | 30.0 |

COMPARATIVE EXAMPLE 13

Under make-up base sample 3 of Comparative Example 8 was prepared as an under make-up base sample for a first layer. Next, a finishing make-up material sample for a second layer (oily foundation) was prepared in the same manner as in the preparation of finishing make-up material 5 of Comparative Example 12 except that barium sulfate was used in place of aluminum powder. This is called "finishing make-up material sample 6".

All the cosmetic materials samples prepared as above were tested with respect to the masking power for covering and masking skin troubles (as light-shielding power), the lastability of the make-up coat formed and the feeling to the skin in actual application. Evaluation of the test results was effected on the basis of the following criteria.

LIGHT-SHIELDABILITY

Each sample was applied to the faces of five women panelists each having a nevus on her face, in the order of under make-up base sample and finishing make-up material sample so that their faces were made up. The colors of the nevus part and the healthy part were measured with a color difference meter (E80 Model, manufactured by Nippon Denshoku Co.), and E was calculated out from the following equation. The value of E indicates how the nevus part became similar to the healthy part by the make-up coat or how the former was covered and masked by the same.

$$\Delta E = ((\Delta L)^2 + (\Delta a)^2 + (\Delta b)^2)^{\frac{1}{2}}$$

Criteria for Evaluation:
⊙ : Excellent (ΔE is less than 1)
○: Good (ΔE is from 1.0 to 1.5)
Δ: Fair (ΔE is from 1.5 to 2.0)
×: Bad (ΔE is more than 2).

LASTABILITY OF MAKE-UP COAT FORMED

Each sample was applied to the faces of five women panelists each having a nevus on her face, in the same order as above, whereupon the lastability of the make-up coat formed was sensually evaluated by them.

Criteria for Evaluation:
⊙ : Excellent
○: Good
Δ: Fair
×: Bad.

OUTWARD APPEARANCE OF MAKE-UP COAT FORMED

Each sample was applied to the faces of five women panelists each having a nevus on her face, in the same order as above, whereupon the outward appearance of the make-up coat formed was visually evaluated by beauty experts.

Criteria for Evaluation:
◉ : Excellent.
○: Good.
△: Fair as the finish coat was somewhat thick and not natural.
×: Bad as the finish coat was very thick and not natural.

All the results thus obtained are shown in Table 26 below. In the table 26, total evaluation was effected on the basis of four ranks of ◉, ○, △ and × in this order, ◉ being the best and × being the worst.

TABLE 26

|  | Examples |  |  |  | Comparative Examples |  |  |  |  |  |
|---|---|---|---|---|---|---|---|---|---|---|
|  | 8 | 9 | 10 | 11 | 8 | 9 | 10 | 11 | 12 | 13 |
| Light-shieldability | ◉ | ○ | ◉ | ○ | △ | △ | △ | △ | △ | × |
| Lastability | ○ | ○ | ◉ | ○ | △ | ○ | △ | × | △ | △ |
| Outward Appearance | ○ | ○ | ◉ | ◉ | ○ | ○ | ○ | ○ | △ | × |
| Total Evaluation | ◉ | ○ | ◉ | ○ | △ | △ | △ | △ | △ | × |

We claim:

1. A double-coat type make-up cosmetic product comprising a combination of:

(A) an under make-up base forming a first layer, said first layer consisting essentially of (1) 0.5 to 70% by weight of an adhesive film-forming agent and (2) a diluent forming the balance of said first layer, wherein said film-forming agent is selected from the group consisting of:

(i) an acrylic copolymer having a mean molecular weight of 10,000 to 1,000,000 as prepared by the copolymerization of an acrylate as a main monomer component and 1 to 10% by weight, based on the main monomer component, of a polymerizing carboxylic acid as a side monomer component;

(ii) an acrylic copolymer having a mean molecular weight of 10,000 to 1,000,000 as prepared by the copolymerization of an acrylate as a main monomer component, a first side monomer component selected from the group consisting of vinyl acetate, methyl methacrylate, and acrylamide, and 1 to 10% by weight, based on the total weight of the main monomer component and the first side monomer component, of a polymerizing carboxylic acid as a second side monomer component; and (iii) a three dimensional network structure silicone, and wherein said diluent is water when said film-forming agent is the copolymer in (i) or (ii), and said diluent is selected from the group consisting of a volatile silicone oil and a liquid hydrocarbon when said film-forming agent is a three-dimensional network structure silicone; and (B) a finishing make-up material forming a second layer, said second layer containing from 5 to 100% by weight of an aluminum powder.

2. The double-coat type make-up cosmetic product as claimed in claim 1, in which the main monomer component in the copolymer in (i) and (ii) is at least one selected from the group consisting of methyl acrylate, ethyl acrylate, propyl acrylate, butyl acrylate, isobutyl acrylate, hexyl acrylate and 2-ethylhexyl acrylate, and the side monomer component in the copolymer in (i) or the second side monomer component in the copolymer in (ii) is at least one selected from the group consisting of acrylic acid, methylacrylic acid itaconic acid and maleic acid.

3. The double-coat type make-up cosmetic product as claimed in claim 1, in which the ratio of the main monomer component to the first side monomer component in the copolymer in (ii) is from 99/1 to 70/30 by weight.

4. The double-coat type make-up cosmetic product as claimed in claim 1, in which the aluminum powder has a mean grain size of falling within the range of from 10 to 70 μm.

5. The double-coat type make-up cosmetic product as claimed in claim 1, in which the content of the aluminum powder falls within the range of from 5 to 40% by weight.

* * * * *